(12) United States Patent
May et al.

(10) Patent No.: US 8,828,012 B2
(45) Date of Patent: Sep. 9, 2014

(54) ANTERIOR CORTEX REFERENCING EXTRAMEDULLARY FEMORAL CUT GUIDE

(75) Inventors: Justin J. May, Leesburg, IN (US); Jason F. Detweiler, Warsaw, IN (US)

(73) Assignee: Zimmer, Inc., Warsaw, IN (US)

(*) Notice: Subject to any disclaimer, the term of this patent is extended or adjusted under 35 U.S.C. 154(b) by 681 days.

(21) Appl. No.: 12/396,135

(22) Filed: Mar. 2, 2009

(65) Prior Publication Data

US 2010/0222783 A1 Sep. 2, 2010

(51) Int. Cl.
*A61B 17/90* (2006.01)
*A61B 17/15* (2006.01)

(52) U.S. Cl.
CPC .................................. *A61B 17/155* (2013.01)
USPC ........................................................ 606/88

(58) Field of Classification Search
USPC ................... 606/87–89, 86 R, 96–98
See application file for complete search history.

(56) References Cited

U.S. PATENT DOCUMENTS

| 4,646,729 | A | | 3/1987 | Kenna et al. | |
| 5,002,547 | A | | 3/1991 | Poggie et al. | |
| 5,037,423 | A | | 8/1991 | Kenna | |
| 5,486,178 | A | * | 1/1996 | Hodge | 606/82 |
| 5,624,444 | A | | 4/1997 | Wixon et al. | |
| 5,649,929 | A | * | 7/1997 | Callaway | 606/88 |
| 5,743,915 | A | | 4/1998 | Bertin et al. | |
| 5,810,831 | A | | 9/1998 | D'Antonio | |
| 6,056,756 | A | | 5/2000 | Eng et al. | |
| 6,290,704 | B1 | | 9/2001 | Burkinshaw et al. | |
| 6,458,135 | B1 | | 10/2002 | Harwin et al. | |
| 6,500,179 | B1 | * | 12/2002 | Masini | 606/88 |
| 6,575,980 | B1 | * | 6/2003 | Robie et al. | 606/88 |
| 6,979,299 | B2 | | 12/2005 | Peabody et al. | |
| 7,115,133 | B2 | | 10/2006 | Plumet et al. | |
| 2003/0028196 | A1 | * | 2/2003 | Bonutti | 606/87 |
| 2004/0102786 | A1 | * | 5/2004 | Grundei | 606/88 |
| 2006/0142778 | A1 | | 6/2006 | Dees, Jr. | |
| 2006/0200163 | A1 | * | 9/2006 | Roger et al. | 606/89 |
| 2007/0173848 | A1 | * | 7/2007 | Lennox et al. | 606/87 |
| 2007/0282451 | A1 | * | 12/2007 | Metzger et al. | 623/20.28 |

* cited by examiner

*Primary Examiner* — Kevin T Truong
*Assistant Examiner* — Zade Coley
(74) *Attorney, Agent, or Firm* — Schwegman Lundberg & Woessner, P.A.

(57) ABSTRACT

An apparatus and method are provided for aligning an extramedullary femoral cut guide by referencing the anterior cortex of a femur. An anterior cortex referencing extramedullary femoral cut guide is provided to guide an osteotomy device to prepare the femur to receive a prosthesis. An alignment gauge is included in the cut guide to determine proper and improper alignment of the cut guide with respect to the anterior cortex of the femur.

21 Claims, 5 Drawing Sheets

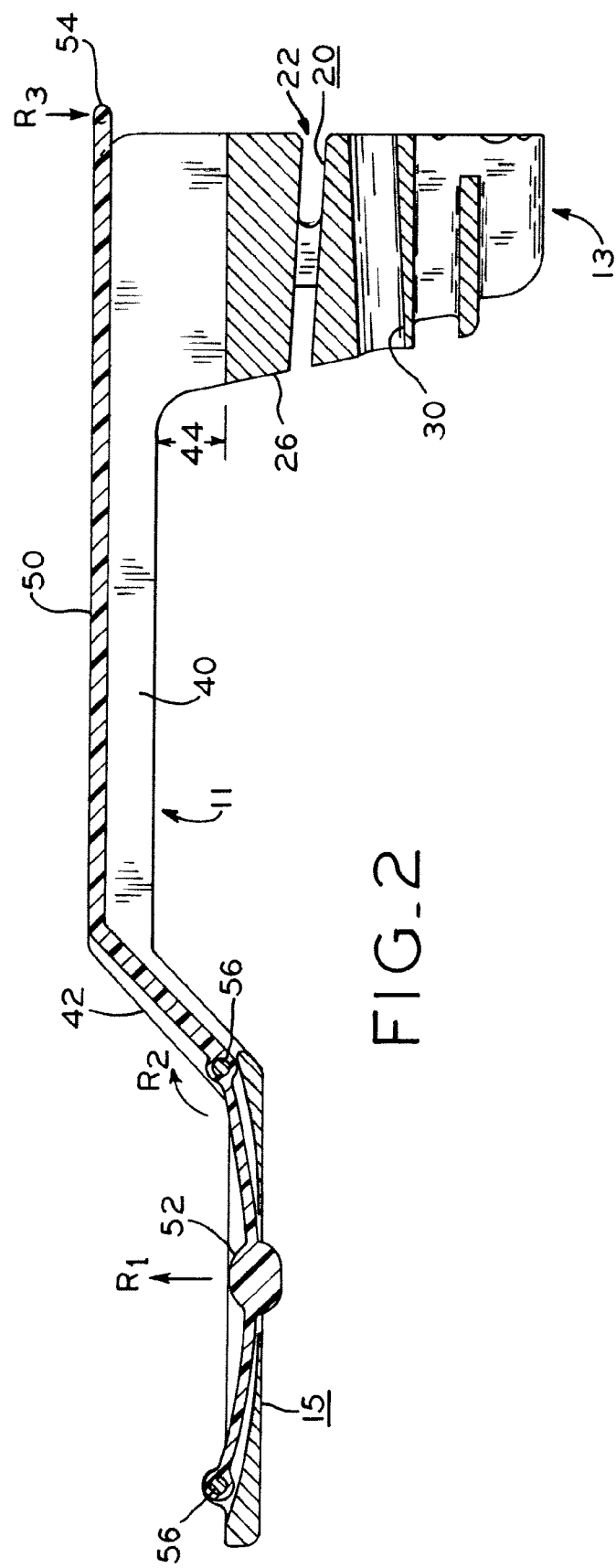
FIG._2

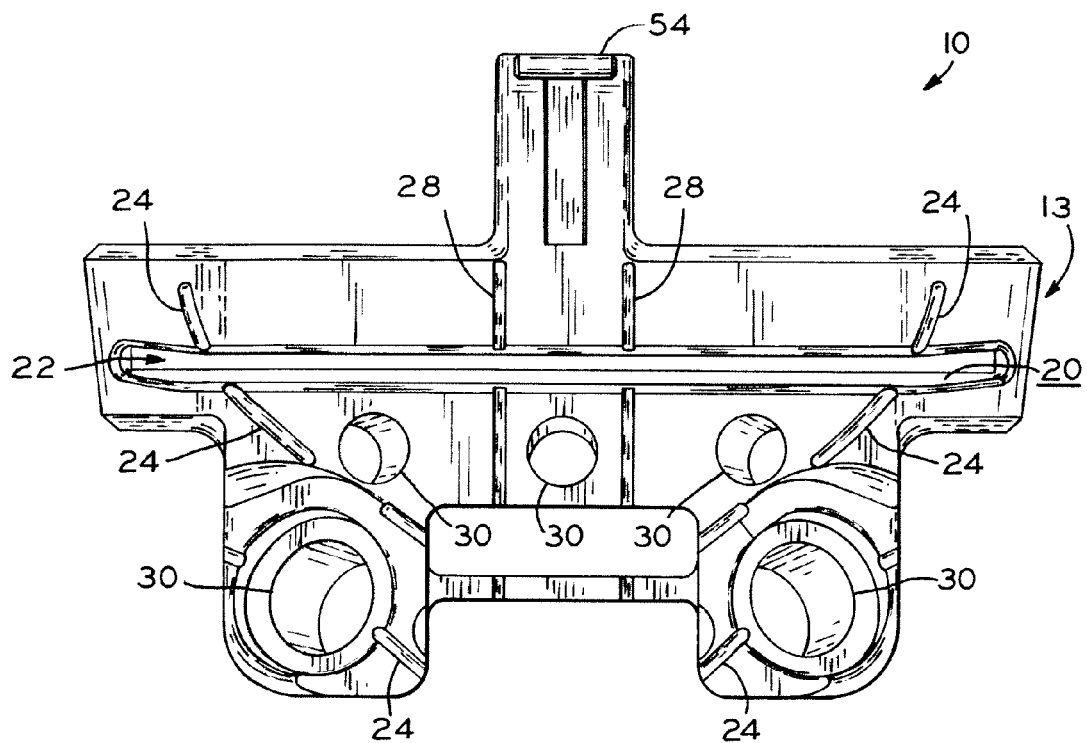
FIG_3
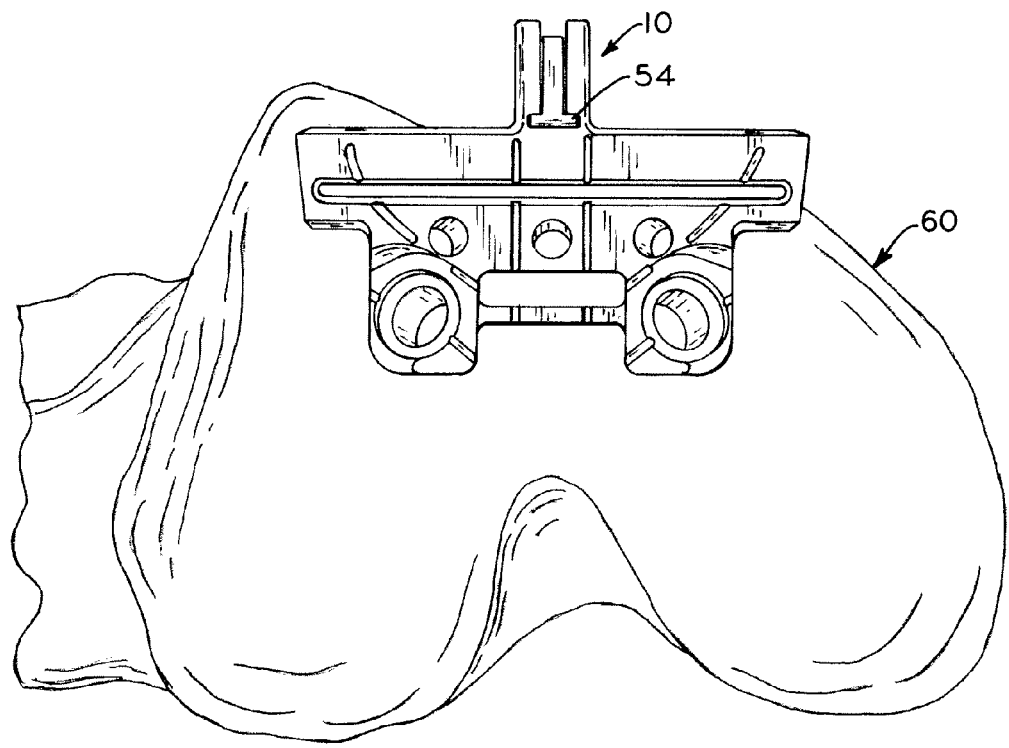
FIG_4

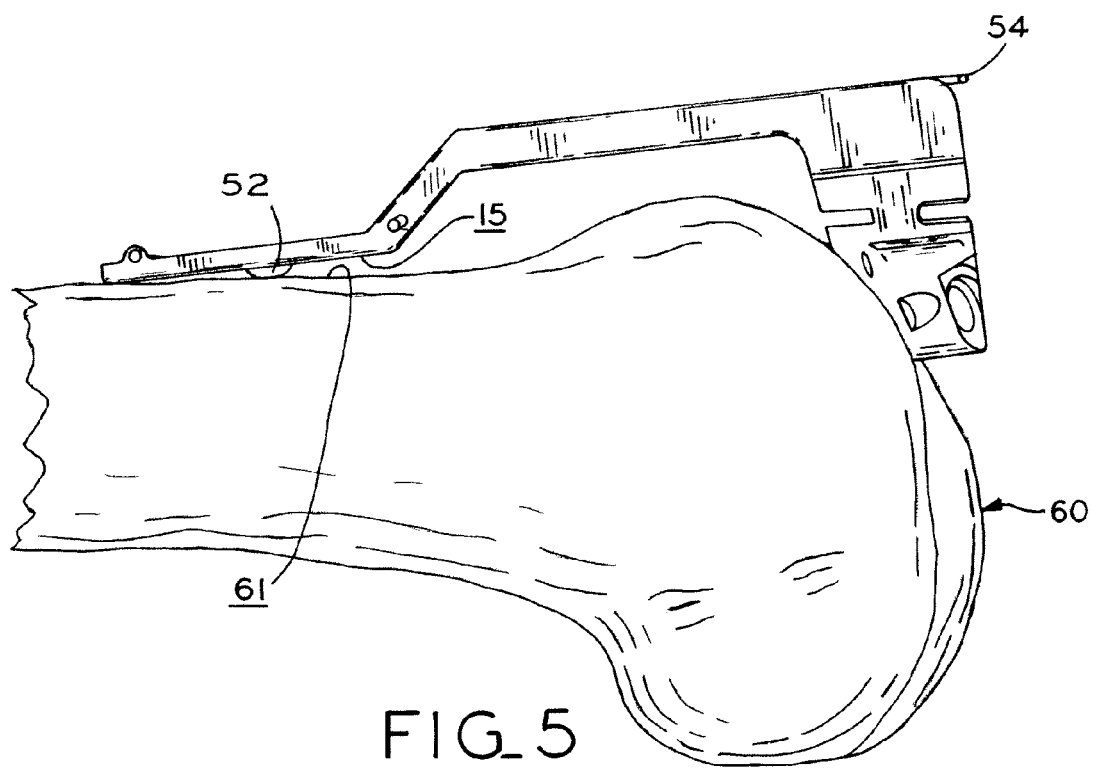
FIG_5
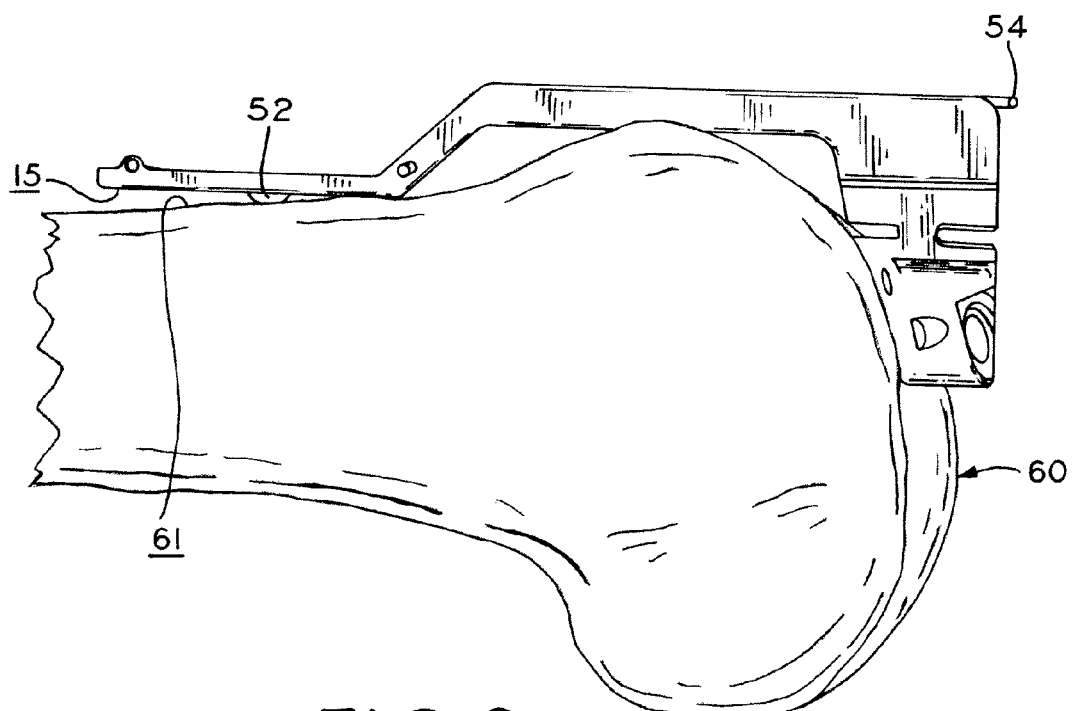
FIG_6

ANTERIOR CORTEX REFERENCING EXTRAMEDULLARY FEMORAL CUT GUIDE

BACKGROUND

1. Field of the Invention

The present invention relates to an instrument for use in orthopedic procedures. More specifically, the invention relates to an anterior cortex referencing extramedullary femoral cut guide.

2. Description of the Prior Art

Methods and apparatuses have been developed to assist a surgeon in performing a femoral osteotomy in knee arthroplasty procedures. One such method references the intramedullary cavity of the femur when aligning a femoral cut guide. In this method, an intramedullary rod is inserted into the intramedullary cavity of the femur to act as a reference and a base for a cutting guide.

SUMMARY

An apparatus and method are provided for aligning an extramedullary femoral cut guide by referencing the anterior cortex of a femur. An anterior cortex referencing extramedullary femoral cut guide is provided to guide an osteotomy device to prepare the femur to receive a prosthesis. An alignment gauge is included in the cut guide to determine proper and improper alignment of the cut guide with respect to the anterior cortex of the femur.

One or more of the embodiments of the present invention includes a cut guide, comprising a guide having a guide surface adapted for guiding an osteotomy device, and a boom extending from the guide, the boom including an anterior reference surface, the anterior reference surface being substantially planar, wherein the anterior reference surface and the guide surface are oriented relative to each other such that when the anterior reference surface is positioned flush against an anterior cortex of a femur, the guide surface is aligned to guide the osteotomy device to prepare the femur to receive a prosthesis.

In one form thereof, the present invention provides a cut guide, comprising a guide having a guide surface for guiding an osteotomy device, and reference means for referencing an anterior cortex of a femur to align a trajectory of the guide surface to properly guide the osteotomy device to prepare the femur to receive a prosthesis.

In another form thereof, the present invention provides a method for aligning an osteotomy device in a knee arthroplasty procedure, including the steps of: providing a cut guide, comprising a guide having a guide surface adapted for guiding an osteotomy device, and a boom extending from the guide, the boom including an anterior reference surface being substantially planar, wherein the anterior reference surface and the guide surface are oriented relative to each other such that when the anterior reference surface is positioned flush against an anterior cortex of a femur, the guide surface is aligned to guide the osteotomy device to prepare the femur to receive a prosthesis; and aligning the cut guide to guide the osteotomy device to prepare the femur to receive a prosthesis by placing the anterior reference surface flush against the anterior cortex of the femur such that the guide surface is aligned to guide the osteotomy device to prepare the femur to receive a prosthesis.

BRIEF DESCRIPTION OF THE DRAWINGS

The above-mentioned and other features and advantages of this invention, and the manner of attaining them, will become more apparent and the invention itself will be better understood by reference to the following descriptions of embodiments of the invention taken in conjunction with the accompanying drawings, wherein:

FIG. 2 is a cross-sectional view of the cut guide taken along line 2-2 of FIG. 1;

FIG. 3 is a plan view of the cut guide of FIG. 1;

FIG. 4 is a plan view of the cut guide of FIG. 1 properly aligned with a femur to guide an osteotomy device thereof;

FIG. 5 is an elevational view of the cut guide of FIG. 1 misaligned with the anterior cortex of a femur;

FIG. 6 is an elevational view of the cut guide of FIG. 1 misaligned with the anterior cortex of a femur.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
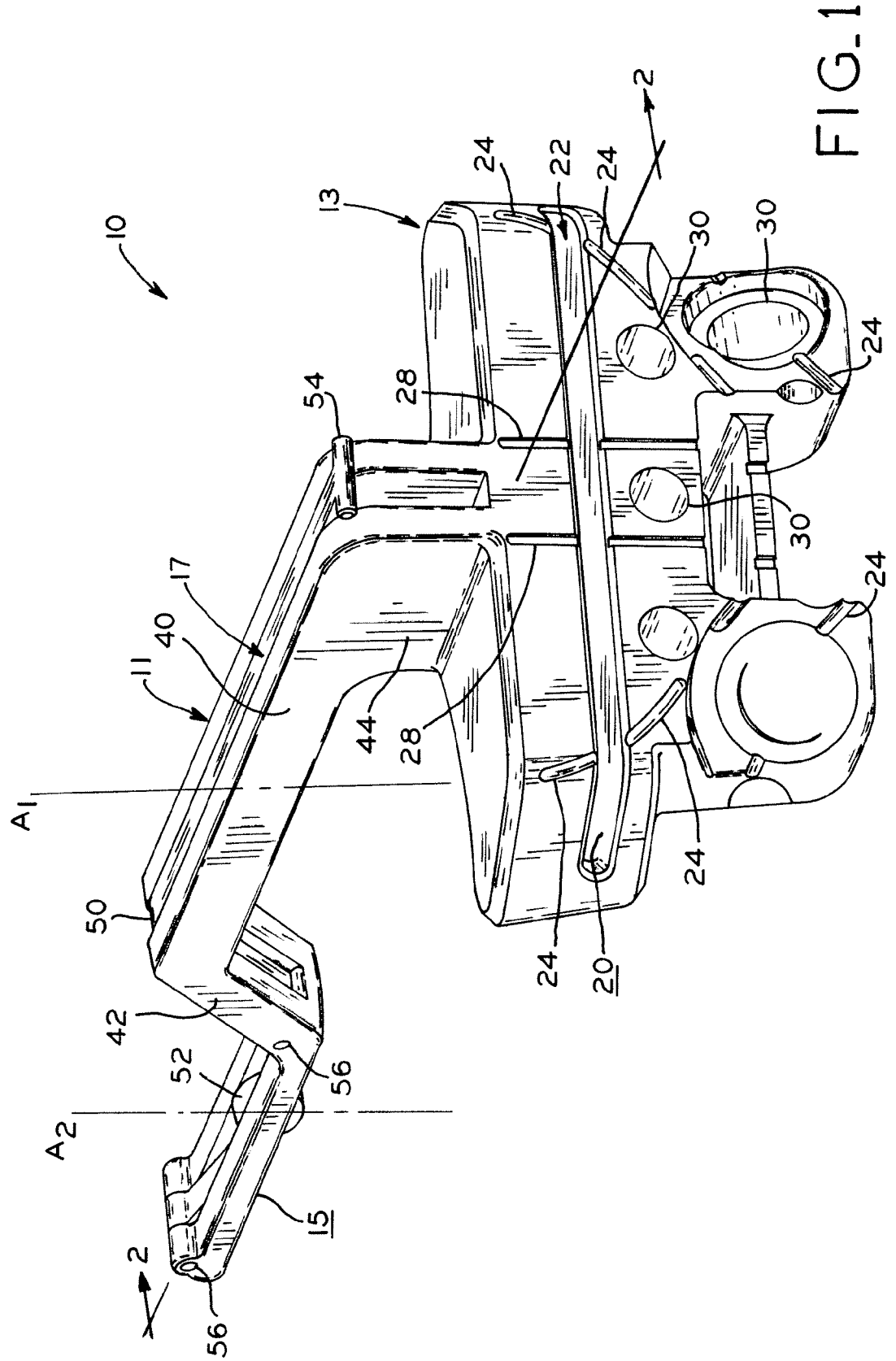
FIG. 1 is a perspective view of a cut guide.

FIG. 1 is a perspective view of cut guide 10. Cut guide 10 includes boom 11, guide 13, anterior reference surface 15, and alignment gauge 17. Boom 11, guide 13, and anterior reference surface 15 form an integral, monolithic structure. Boom 11 of cut guide 10 comprises a U-shaped boom having base 40 and a pair of upstanding arms connected to base 40. Boom 11 includes first upstanding arm 42 and second upstanding arm 44. Guide 13 is connected to boom 11 at second upstanding arm 44 of boom 11. Guide 13 includes guide surface 20, cut slot 22, medial/lateral alignment indicators 24, alignment markers 28, and pin holes 30. Anterior reference surface 15 is connected to boom 11 at first upstanding arm 42 of boom 11. Cut guide 10 is structured this way so there is room to position boom 11 away from the anterior condyles and/or the anterior surface of femur 60 that forms the sulcus while allowing cut guide 10 to be properly aligned on the distal end of femur 60. Guide surface 20, once aligned, guides an osteotomy device to prepare femur 60 to receive a prosthesis.

Alignment gauge 17 includes flexible member 50, bulb 52, indicator 54, and pins 56. Bulb 52 of alignment gauge 17 is connected to flexible member 50. Indicator 54 is also connected to flexible member 50 and indicator 54 is positioned adjacent second upstanding arm 44 and base 40 when in an original position. Indicator 54 is adjacent second upstanding arm 44 and guide 13 when in an aligned position. Flexible member 50 of alignment gauge 17 is connected to anterior reference surface 15 of boom 11 via a pair of pins 56. Alignment gauge 17 determines the alignment of cut guide 10 with respect to anterior cortex 61 of femur 60, as discussed below.

In operation, cut guide 10 is aligned to guide an osteotomy device in a knee arthroplasty procedure. Guide surface 20 of guide 13 of cut guide 10 is adapted for guiding an osteotomy device. Knee arthroplasty procedures include total knee arthroplasty, partial knee arthroplasty, and patello-femoral arthroplasty. In use, anterior reference surface 15 of cut guide 10, which is substantially planar, is placed on anterior cortex 61, in FIGS. 5-7, of femur 60 with guide 13 positioned at the distal end of femur 60. More specifically, anterior reference surface 15 is placed on the diaphysis of femur 60. While anterior reference surface 15 of cut guide 10 is referenced and described herein with specific reference to placement on the diaphysis, in other exemplary embodiments, anterior reference surface 15 of cut guide 10 can be placed on other portions of the bone, such as the metaphysis. In positioning guide 13 at the distal end of femur 60, distal femoral surface 26, shown in FIG. 2, is placed adjacent femur 60. In the aligned position illustrated in FIG. 7, boom 11 is substantially parallel with and spaced a distance from femur 60. Boom 11 lays through the sulcus of femur 60 when in this position. Anterior reference surface 15 and guide surface 20 are oriented relative to each other such that when anterior reference surface 15 is positioned flush against anterior cortex 61 of femur 60, guide surface 20 is aligned to guide an osteotomy, such as an oscillating saw, device to prepare femur 60 to receive a prosthesis.

Figure 7:
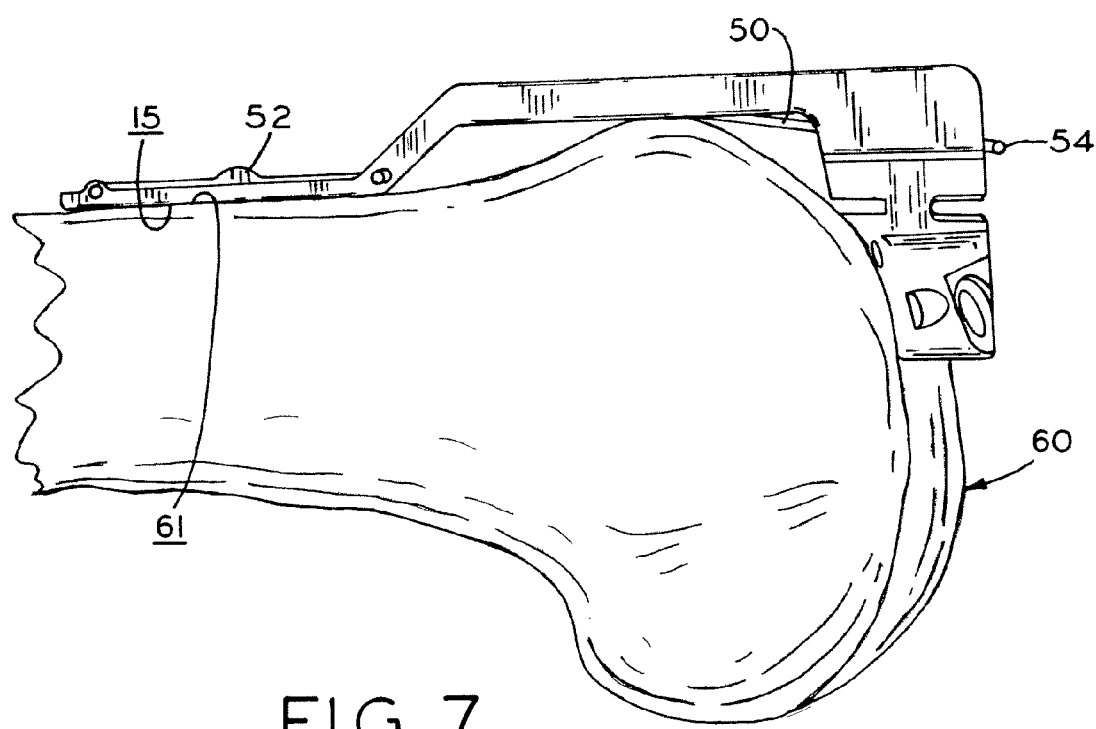
FIG. 7 is an elevational view of the cut guide of FIG. 1 positioned in proper alignment on the anterior cortex of a femur.

In operation, alignment gauge 17 determines whether there is proper or improper alignment of cut guide 10 on anterior cortex 61 of femur 60. Alignment gauge 17 functions by the use of a leaf spring arrangement, including bulb 52, flexible member 50, and pins 56, which operate together while connected to anterior reference surface 15. Alignment gauge 17 can be made of any known orthopedic biocompatible material or biocompatible polymer, such as 304 stainless steel or polyetheretherketone (PEEK). To determine whether alignment is proper or improper, the user checks the position of indicator 54 adjacent second upstanding arm 44 and guide 13. When the substantially planar surface of anterior reference surface 15 is placed flush against anterior cortex 61 of femur 60, bulb 52 is displaced away from anterior cortex 61 of femur 60 in direction $R_1$, shown in FIG. 2, and flexible member 50 of alignment gauge 17 rotates about pin 56 in direction $R_2$, shown in FIG. 2. When alignment is proper, this displacement in direction $R_1$ and $R_2$ causes indicator 54 to move into an aligned position adjacent guide 13 in direction $R_3$, which is shown in FIGS. 4 and 7. Cut guide 10 becomes aligned properly on anterior cortex 61 of femur 60 when distal femoral surface 26, shown in FIG. 2, is adjacent the distal end of femur 60; anterior reference surface 15 is flush against the anterior cortex 61; and bulb 52 of alignment gauge 17 is displaced away from anterior cortex 61 of femur 60 in direction $R_1$, as shown in FIG. 7. When bulb 52 of alignment gauge 17 is displaced away from anterior cortex 61 of femur 60 in direction $R_1$, flexible member 50 of alignment gauge 17 is biased downwardly toward guide 13 in direction $R_2$, shown in FIG. 2, and the position of indicator 54 moves in direction $R_3$, which indicates proper alignment, as shown in FIGS. 4 and 7. Alternatively, as a back up to alignment gauge 17, the user could reach to anterior reference surface 15 while positioned on anterior cortex 61 of femur 60 and digitally palpate bulb 52 to determine proper alignment of cut guide 10.

Improper alignment is shown by indicator 54 when indicator 54 remains in its original position, as seen in FIGS. 1, 2, 5 and 6. Indicator 54 remains in its original position when anterior reference surface 15 is placed against anterior cortex 61 of femur 60, but is not flush with anterior cortex 61. When bulb 52 and anterior reference surface 15 are in contact with anterior cortex 61 of femur 60 and bulb 52 remains in its original position or is only slightly displaced in direction $R_1$, indicator 54 will not move from its original position, or indicator 54 will slightly move from its original position in direction $R_3$ due to cut guide 10 being misaligned with respect to femur 60. Improper position is also shown by indicator 54 when it is positioned anywhere between the proper alignment position, shown in FIGS. 4 and 7, and the original rest position of indicator 54 in direction $R_3$ shown in FIG. 3. This occurs when anterior reference surface 15 is not in flush contact with anterior cortex 61 of femur 60 and bulb 52 is only slightly displaced in direction $R_1$ causing indicator 54 to move only slightly from its original position in direction $R_3$ due to cut guide 10 being misaligned with respect to femur 60.

In another embodiment of the present invention, alignment gauge 17 includes a plurality of bulbs 52. The addition of a second bulb 52 would provide the user with more immediate visual feedback as to proper and improper alignment of cut guide 10. This embodiment would also allow for additional tactile feedback when digitally palpating bulbs 52 as the back up method to observing alignment gauge 17.

In another embodiment of the present invention, alignment gauge 17 measures the angular variation between anterior cortex 61 of femur 60 and anterior reference surface 15. This is beneficial in cases where there is an angular discrepancy between the anatomical axis of femur 60 and anterior cortex 61 which prevents anterior cortex 61 from providing a proper reference point (i.e., will not allow for proper alignment of cut guide 10). A proper reference point is present when anterior cortex 61 is substantially parallel to the anatomical axis of femur 60. In certain instances, a pre-operative X-ray may show an angle between anterior cortex 61 and the anatomical axis of femur 60 of sufficient magnitude that the user feels that anterior cortex 61 no longer provides a proper reference point. When this occurs, alignment gauge 17 may indicate the proper angular variation between anterior reference surface 15 and anterior cortex 61 to offset the angular variation between anterior cortex 61 and the anatomical axis of femur 60 and allow for proper positioning of cut guide 10. To achieve this, the user positions anterior reference surface 15 substantially parallel with the anatomical axis of femur 60 such that the proximal end of anterior reference surface 15 contacts the bone. Once positioned, bulb 52 contacts anterior cortex 61 and is displaced away from anterior cortex 61 in direction $R_1$, seen in FIG. 2, which then displaces flexible member 50 in direction $R_2$ and indicator 54 in direction $R_3$. As the position of bulb 52 varies along anterior cortex 61, indicator 54 will indicate the various angle variations between anterior cortex 61 and anterior reference surface 15 via markings on guide 13 Guide 13 is marked so that the user can determine the angular variation between anterior cortex 61 and anterior reference surface 15. These markings can be made in one degree increments or any other incremental values.

FIG. 2 is a cross-sectional view of cut guide 10 taken along line 2-2 of FIG. 1. Alignment gauge 17 includes flexible member 50, bulb 52, indicator 54, and pins 56. Flexible member 50 is a continuous member that includes bulb 52 and indicator 54. Flexible member 50 is connected to an end of anterior reference surface 15 and first upstanding arm 42 via pins 56. Alignment gauge 17 operates to determine proper or improper alignment of cut guide 10 to guide an osteotomy device to prepare the femur to receive a prosthesis, as discussed above.

FIG. 3 is a plan view of cut guide 10 of FIG. 1 showing indicator 54 in its original position. Guide 13 includes guide surface 20, cut slot 22, medial/lateral alignment indicators 24, alignment marker 28, and pin holes 30. Cut slot 22 is used to guide an osteotomy device through guide 13 of cut guide 10. Osteotomy devices, such as oscillating saws, are inserted through cut slot 22, and adjacent to guide surface 20, to osteotomize femur 60 in a knee arthroplasty procedure. When cut guide 10 is properly aligned, medial/lateral alignment indicators 24 represent the proper location of where the proximal tibia contacts the distal end of femur 60 in full extension. Medial/lateral alignment indicators 24 are used as guides for the outer profile of knee implants relative to the location where the proximal tibia contacts the distal end of femur 60. If cut guide 10 is not properly aligned on anterior cortex 61 of femur 60 then medial/lateral alignment indicators 24 will not represent the proper location of where the proximal tibia contacts the distal end of femur 60 in full extension. Medial/lateral alignment indicators 24 assist in aligning cut guide 10, and determine the proper location where the proximal tibia contacts the distal end of femur 60, by rotating cut guide 10 relative to any axis that is substantially perpendicular to guide surface 20, such as axis $A_1$ or $A_2$ shown in FIG. 1, when anterior reference surface 15 of cut guide 10 is flush with anterior cortex 61 of femur 60. The user can rotate cut guide 10 along an axis that is substantially perpendicular to guide surface 20, such as axis $A_1$ or $A_2$, shown in FIG. 1, while anterior reference surface 15 is still flush with anterior cortex 61 of femur 60, to properly position cut guide 10 in medial/lateral alignment with femur 60. While referred to as medial/lateral alignment indicators 24, medial/lateral alignment indicators 24 may also act to provide an anterior/posterior reference point for the placement of an implant on the distal end of a resected femur. Alignment marker 28 of guide 13 can also be used to determine whether cut guide 10 is aligned substantially parallel a Whiteside's line. Pin holes 30 are used to secure cut guide 10 to femur 60 once cut guide 10 is properly aligned. This can be done with pins, screws, or any other surgical device known in the art.

FIGS. 4-7 show cut guide 10 placed on femur 60 in various alignments. FIGS. 4 and 7 show proper alignment of cut guide 10 with anterior cortex 61 of femur 60 while FIGS. 5 and 6 show improper alignment of cut guide 10 with anterior cortex 61 of femur 60.

FIG. 4 shows a front view of cut guide 10 positioned on anterior cortex 61 of femur 60 with indicator 54 showing proper alignment. As mentioned above, in order to determine proper alignment of cut guide 10, the user checks the position of indicator 54 adjacent second upstanding arm 44 and guide 13. When the substantially planar surface of anterior reference surface 15 is placed flush against anterior cortex 61 of femur 60, bulb 52 is displaced away from anterior cortex 61 of femur 60 in direction $R_1$, shown in FIG. 2, and flexible member 50 of alignment gauge 17 is displaced in direction $R_2$ causing indicator 54 of alignment gauge 17 to be biased downwardly toward guide 13 in direction $R_3$ toward guide 13. The displacement in direction $R_1$ causes flexible member 50 to move in direction $R_2$ causing indicator 54 to move in direction $R_3$ into an aligned position. Cut guide 10 becomes aligned properly on the anterior cortex 61 of the femur 60 when distal femoral surface 26, shown in FIG. 2, is adjacent the distal end of femur 60, and anterior reference surface 15 is flush against the anterior cortex 61, causing bulb 52 of alignment gauge 17 to be displaced away from anterior cortex 61 of femur 60 in direction $R_1$.

FIG. 5 shows an elevational view of cut guide 10 misaligned with anterior cortex 61 of femur 60. When cut guide 10 is misaligned with anterior cortex 61 of femur 60, indicator 54 will be in a position that shows improper alignment. As mentioned above, improper alignment is shown by indicator 54 when indicator 54 remains in its original position. Indicator 54 remains in its original position when anterior reference surface 15 is not flush against anterior cortex 61 of femur 60. When the substantially planar surface of anterior reference surface 15 is in contact with anterior cortex 61 of the femur 60, but not flush against anterior cortex 61 of femur 60, indicator 54 will not move away from its original position in direction $R_3$ due to cut guide 10 being misaligned on the anterior cortex 61 of femur 60. Improper position is also shown by indicator 54 when it is positioned anywhere between the proper alignment position in direction $R_3$, shown in FIGS. 4 and 7, and the original rest position of indicator 54, shown in FIG. 3. This occurs when bulb 52 and anterior reference surface 15 are in contact with the anterior cortex 61 of the femur 60 and bulb 52 is only slightly displaced in direction $R_1$ causing indicator 54 to move only slightly from its original position in direction $R_3$ due to cut guide 10 being misaligned with respect to femur 60.

FIG. 6 shows another elevational view of cut guide 10 misaligned with anterior cortex 61 of femur 60. As mentioned above, improper alignment is shown by indicator 54 when indicator 54 remains in its original position. Indicator 54 remains in its original position when anterior reference surface 15 is placed against, but is not flush with, anterior cortex 61 of femur 60. When bulb 52 and the substantially planar anterior reference surface 15 are in contact with anterior cortex 61 of femur 60, and are not flush against anterior cortex 61, and bulb 52 remains in its original position, indicator 54 will not move away from its original position in direction $R_3$ due to cut guide 10 being misaligned on anterior cortex 61 of femur 60. Improper position is also shown by indicator 54 when it is positioned anywhere between the proper alignment position in direction $R_3$, shown in FIGS. 4 and 7, and the original rest position of indicator 54, shown in FIG. 3. This occurs when bulb 52 and anterior reference surface 15 are in contact with anterior cortex 61 of femur 60 and bulb 52 is only slightly displaced in direction $R_1$ causing indicator 54 to move only slightly from its original position in direction $R_3$ due to cut guide 10 being misaligned with respect to femur 60.

FIG. 7 shows an elevational view of indicator 54 of cut guide 10 positioned in proper alignment on anterior cortex 61 of femur 60. As mentioned above, in order to determine proper alignment of cut guide 10, the user checks the position of indicator 54 adjacent second upstanding arm 44 and guide 13. When the substantially planar surface of anterior reference surface 15 is placed flush against anterior cortex 61 of femur 60, bulb 52 is displaced away from anterior cortex 61 of femur 60 in direction $R_1$ and flexible member 50 is displaced in direction $R_2$ causing indicator 54 of alignment gauge 17 to be biased downwardly toward guide 13 in direction $R_3$. This displacement in direction $R_3$ causes the maximum travel possible by indicator 54.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A cut guide, comprising:
    a guide having a guide surface adapted for guiding an osteotomy device;
    an anterior reference surface spaced from said guide, said anterior reference surface being substantially planar and having a predefined orientation relative to said guide surface;
    a boom including a pair of upstanding arms and a base, spanning said upstanding arms, the upstanding arms oriented in a raised direction relative to said guide and said anterior reference surface forming an offset of said base from both said guide and said anterior reference surface; and
    an alignment gauge including a flexible member coupled to said boom at first and second distal to medial spaced locations, having a portion extending beyond the anterior reference surface in a natively biased position, and an indicator, extending from said flexible member and moveable from a first position, indicative of said flexible member portion maintaining said natively biased position, to a second position, indicative of the anterior reference surface being positioned flush with a surface of a bone.

2. The cut guide of claim 1, wherein said guide is connected to a first one of said pair of upstanding arms and said anterior reference surface is connected to a second one of said pair of upstanding arms.

3. The cut guide of claim 1, wherein said boom, said guide, and said anterior reference surface form an integral, monolithic structure.

4. The cut guide of claim 1, wherein said alignment gauge further comprises a bulb connected to said flexible member, said bulb extending beyond the anterior reference surface in said natively biased position.

5. The cut guide of claim 1, wherein the first and second distal to medial spaced locations bound said portion extending beyond said anterior reference surface in said natively biased position.

6. The cut guide of claim 5, wherein the coupling between said flexible member and said boom at said first or second location includes a pivot connection, about which said flexible member pivots as said indicator moves between said first position and said second position.

7. The cut guide of claim 1, wherein said pair of upstanding arms and said base form a U-shape.

8. The cut guide of claim 1, wherein said base is offset from said guide and said anterior reference surface in both said raised direction and a lateral direction relative to said guide and said anterior reference surface.

9. The cut guide of claim 1, wherein said boom is U-shaped, including a channel extending substantially along its length including and said flexible member is disposed within and extending the length of said channel.

10. The cut guide of claim 1, wherein said guide includes a medial or lateral alignment indicator.

11. A cut guide, comprising:
a guide having a guide surface adapted for guiding an osteotomy device;
an anterior reference surface spaced from said guide, said anterior reference surface being substantially planar and having a predefined orientation relative to said guide surface;
a boom including a channel extending substantially along its length, a pair of upstanding arms, and a base spanning said upstanding arms, said upstanding arms oriented in a raised direction relative to said guide and said anterior reference surface forming an offset of said base from both said guide and said anterior reference surface; and
an alignment means including a flexible member, disposed within and extending the length of said channel and having a portion extending beyond the anterior reference surface, in a natively biased position and an indicator, extending from said flexible member and moveable from a first position, indicative of said flexible member portion maintaining said natively biased position, to a second position, indicative of the anterior reference surface being positioned flush with a surface of a bone.

12. The cut guide of claim 11, wherein said guide is connected to a first one of said-pair of upstanding arms and said anterior reference surface is connected to a second one of said pair of upstanding arms.

13. The cut guide of claim 11, wherein said boom, said guide, and said anterior reference surface form an integral, monolithic structure.

14. The cut guide of claim 11, wherein said alignment means further comprises a bulb connected to said flexible member, said bulb extending beyond the anterior reference surface in the natively biased position.

15. The cut guide of claim 11, wherein said flexible member is coupled to said boom at first and second spaced locations, which bound said portion extending beyond said anterior reference surface in said natively biased position.

16. The cut guide of claim 15, wherein the coupling between said flexible member and said boom at said first or second location includes a pivot connection, about which said flexible member pivots as said indicator moves between said first position and said second position.

17. The cut guide of claim 15, wherein one of said upstanding arms includes one of the first and second spaced locations.

18. The cut guide of claim 11, wherein said boom is U-shaped.

19. The cut guide of claim 11, wherein said base is offset from said guide and said anterior reference surface in both said raised direction and a lateral direction relative to said guide and said anterior reference surface.

20. The cut guide of claim 11, wherein said guide includes a medial or lateral alignment indicator.

21. A cut guide, comprising:
a guide having a guide surface adapted for guiding an osteotomy device;
an anterior reference surface spaced from said guide, said anterior reference surface being substantially planar and having a predefined orientation relative to said guide surface;
a boom including a pair of upstanding arms and a base, spanning said upstanding arms, the upstanding arms oriented in a raised direction relative to said guide and said anterior reference surface forming an offset of said base from both said guide and said anterior reference surface; and
an alignment gauge including a flexible member coupled to said boom at first and second locations, said flexible member including a portion extending beyond the anterior reference surface in a natively biased position, the first and second locations configured to bound said portion extending beyond said anterior reference surface in said natively biased position, and an indicator, extending from said flexible member and moveable from a first position, indicative of said flexible member portion maintaining said natively biased position, to a second position, indicative of the anterior reference surface being positioned flush with a surface of a bone,
said first or said second location including a pivot connection, about which said flexible member pivots as said indicator moves between said first position and said second position.

* * * * *